United States Patent
Tachiki et al.

(10) Patent No.: US 7,335,497 B2
(45) Date of Patent: Feb. 26, 2008

(54) PROCESS FOR PRODUCING THEANINE

(75) Inventors: Takashi Tachiki, Kyoto (JP); Yukitaka Okada, Yokkaichi (JP); Makoto Ozeki, Yokkaichi (JP); Tsutomu Okubo, Yokkaichi (JP); Lekh Raj Juneja, Yokkaichi (JP); Nagahiro Yamazaki, Yokkaichi (JP)

(73) Assignee: Taiyokagaku Co., Ltd., Yokkaichi (JP)

( * ) Notice: Subject to any disclaimer, the term of this patent is extended or adjusted under 35 U.S.C. 154(b) by 187 days.

(21) Appl. No.: 10/523,098

(22) PCT Filed: Apr. 22, 2003

(86) PCT No.: PCT/JP03/05077

§ 371 (c)(1),
(2), (4) Date: Oct. 25, 2005

(87) PCT Pub. No.: WO2004/016798

PCT Pub. Date: Feb. 26, 2004

(65) Prior Publication Data

US 2006/0105437 A1 May 18, 2006

(30) Foreign Application Priority Data

Aug. 6, 2002 (JP) .............................. 2002-229026

(51) Int. Cl.
*C12P 13/04* (2006.01)
*C12P 13/14* (2006.01)

(52) U.S. Cl. ..................................... 435/106; 435/110
(58) Field of Classification Search ............... 435/110, 435/106
See application file for complete search history.

(56) References Cited

U.S. PATENT DOCUMENTS 3,721,606 A * 3/1973 Yokatsuka et al. .......... 435/228

FOREIGN PATENT DOCUMENTS

| JP | 5-328986 A1 | 12/1993 |
| JP | 7-055154 B2 | 6/1995 |
| JP | 089364 A * | 4/2001 |

* cited by examiner

Primary Examiner—Herbert J. Lilling
(74) Attorney, Agent, or Firm—Burr & Brown

(57) ABSTRACT

A method for efficiently producing theanine is provided, wherein glutamine and ethylamine are reacted by

*Pseudomonas citronellosis* GEA FERM BP-8353, which is newly separated/selected from natural soil, belongs to the genus, *Pseudomonas*, and the species *citronellosis* and is a theanine producing bacteria with activities of transferring the γ-glutamyl group. Theanine production increased by four times by using glutaminase derived from the bacteria in a mixture of glutamine and ethylamine at a pH in a range of 9-12 in comparison with conventional methods.

4 Claims, 1 Drawing Sheet

PROCESS FOR PRODUCING THEANINE

TECHNICAL FIELD

The present invention relates to new methods of theanine production.

BACKGROUND ART

Theanine is well acknowledged as a main component of green tea flavor substance, and therefore, is an important component of food essence. In addition, γ-glutamyl derivatives including theanine were reported to suppress convulsion induced by caffeine intake (Chem. Parm. Bull., 19(7), 1301-1307 (1971). ibid.19(6), 1257-1261 (1971). ibid.34(7), 3053-3057 (1986). YAKUGAKUZASSHI 95(7), 892-895 (1975) ).

These results suggest that the compounds act on central nervous system, and therefore, these compounds are hoped for useful bioactive substances.

It is a common practice to produce theanine by extracting the substance from dry tea (Gyokuro) leaves. However, theanine is stored in the leaves but only up to 1.5% of the dry weight. In addition, theanine is rapidly degraded in the commercial tea trees by the active photosynthesis, and therefore theanine can hardly be obtained in commercial tea fields. Thus, extraction of theanine from dry tea leaves is recognized an impractical method industrially.

The difficulty in obtaining theanine at the industrial scale lead to development of new production methods such as to synthesize theanine chemically (Chem. Par. Bull., 19(7), 1301-1308 (1971). The chemical synthesis methods, however, include complicated purification steps and do not produce high yield of theanine. An enzymatic method was also reported (JP,H07-55154,B), wherein theanine is synthesized enzymatically from glutamine and ethylamine by exploiting γ-glutamyl group transfer activity of glutaminase However, glutamic acid produced by glutaminase in parallel with theanine makes purification of theanine complicated.

SUMMARY OF THE INVENTION

The present invention was conducted on the background stated above, and aimed to present an efficient theanine production method and to enable production of theanine easy and at an industrially beneficial scale.

The present inventors isolated a new strain of theanine producing bacteria from soil. The bacterial strain contains glutaminase showing higher activity of theanine synthesis and lower activity of glutamic acid synthesis compared to *Pseudomonas nitroreducens* NBRC12694 (JP, 07-55154, B). The present inventors made further investigation based on this finding, and completed the present invention.

The theanine producing bacteria stated above is a new strain, *Pseudomonas citronellosis* GEA(FERM BP-8353): The bacteria is stored in International Patent Organism Depositary (IPOD), AIST Tsukuba Central 6, 1-1, Higashi 1 -chome, Tsukuba-shi, Ibaraki-Ken 305 -8566, Japan, found and identified by the present inventors for the first time.

The present invention provides efficient method to produce theanine, and enables an simple and industrially advantageous production of theanine.

DETAILED DESCRIPTION OF THE INVENTION

Figure 1:
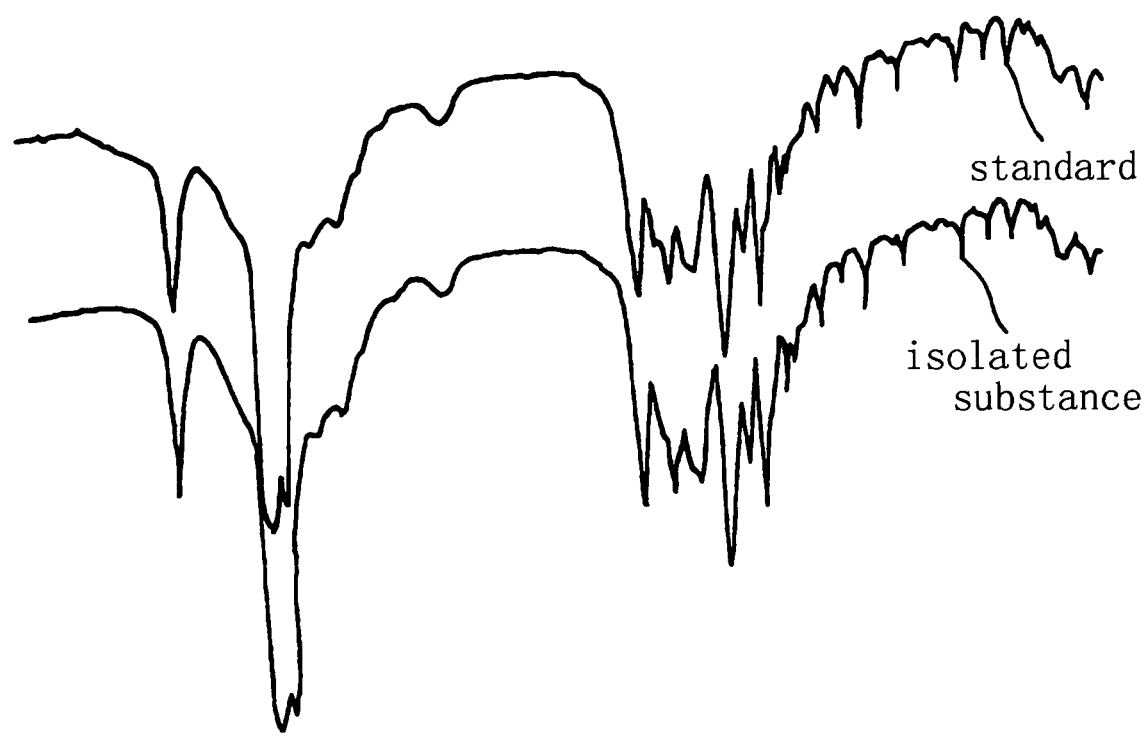
FIG. 1 is an IR spectrum of theanine.

The present invention will be described in detail without intending to restrict the scope of the present invention to the working examples stated below. The present invention can be practiced in various forms without changing the abstract. In addition, the scope of the present invention extends to doctrine of equivalents.

In the present invention, theanine includes γ-glutamyl ethylamide, L-glutamic acid, and γ-ethylamide. Theanine is a component of tea flavor and is used as a food additive to modify the flavor of food.

*Pseudomonas citronellosis* GEA (FERM BP-8353) used in this invention is a new bacterial strain newly isolated by the present inventors. The strain belongs to the genus, *Pseudomonas,* and the species *citronellosis,* and is theanine producing bacteria with activities of transferring γ-glutamyl group. The strain *Pseudomonas citronellosis* GEA was identified by characterization of standard bacterial and biochemical analyses, and by comparison of the DNA sequence coding 16S rRNA to those of other known bacteria.

Glutaminase in the present invention is an enzyme extracted from *Pseudomonas citronellosis* GEA. The sources of the enzymatic activities are live bacterial cells, cell lysates, sonicated cells, chemically lysed cells, lyophilized cells, precipitates with ammonium sulfate, purified enzyme preparations, and other preparations of the bacteria. They can be used as they are and also as fixed forms. For the efficient enzymatic reaction in this invention, the pH 9 to 12 is preferable, and pH 10 to 11 is more preferable. The temperature of the enzymatic reaction is preferably 10 to 55° C., and more preferably 25 to 35° C.

Theanine can be isolated and purified by known methods. For example, theanine can be isolated and purified without any difficulties by combinations of solvent partition, and chromatographies. The details will be described below without intending to restrict the scope of the technology to the examples stated below.

EXAMPLES

Example 1

Isolation of Theanine Utilizing Bacteria

Pieces of soil at Shiga and Kyoto prefectures were collected and soil suspensions were prepared. One hundred strains of theanine utilizing bacteria were isolated by repeating bacterial culture three times serially in a selection medium containing 0.5% theanine, 0.03% yeast extract, 0.05% $KH_2PO_4$, 0.05% $K_2HPO_4$, and 0.03% $MgSO_4 \cdot 7H_2O$ adjusted to pH 7.

Example 2

Preparation of Cell-free Extract

Each of the 100 strains of theanine utilizing bacteria was cultured in 1 liter selection medium stated in Example 1 at 30° C. for 20 hours. The bacterial cells were, then, collected, washed, resuspended in 50 ml phosphate buffer (pH 7.0), and cell-free extract was prepared by sonication at 5° C.~20° C.

Example 3

Enzymatic Reaction

Theanine was synthesized at 30° C. for 2 hours in 100 mM borate buffer (Na$_2$B$_4$O$_7$—NaOH, pH 11) containing 0.3M glutamine, 0.6M ethylamine by using the cell-free extract stated in Example 2.

Example 4

Measurement of Theanine Synthesis and Glutamic Acid Synthesis Activities

Amounts of theanine and glutamic acid synthesized were qualified by diluting the reaction mixture stated in Example 3 appropriately and separated by reverse HPLC. Develosil ODS HG-5 (Nomura Chemicals, Co.Ltd) was used for the analysis, and Water2487 D Dual λUV/VIS Detector (Waters, Co. Ltd) was used as the detector.

Nicotineamide (Nacalai Tesque, Inc.) was used as an internal standard. The mobile phase was a 980:20:1 mixture of deionized water, methanol, and trifluoroacetic acid.

Comparison 1

The activities of theanine and glutamic acid synthesis of newly isolated theanine producing bacteria were compared to *Pseudomonas nitroreducens* using cell-free extracts.

Experiment 1

Selection of Bacterial Strain with High Theanine.Synthesis Activity from the Theanine Producing Bacterial Strains Cell-free extract from each strain cited in Example 1 was prepared as described in Example 2, and enzymatic reaction was done by the method described in Example 3, and amount of theanine synthesized was measured as described in Example 4. As a consequence, a new strain, *Pseudomonas nitroreducens,* containing theanine synthesis activity 4 times higher than the known strain was obtained.

TABLE 1

|  | Theanine synthetic activities | Glutamic acid synthetic activities |
| --- | --- | --- |
| *Pseudomonas nitroreducens* | 2.1 | 2.2 |
| Newly isolated strain | 9.6 | 2.6 |

Unit: mM/(h · mg)

Example 5

Identification of the Newly Isolated Strain

The following factors of the newly isolated strain were characterized according to the protocol of bacteriological and biochemical standards. These were gram staining, cell morphology, catalase test, reducing activity of nitric acid, pyrazinamidase, pyrrolidonyarylamidase, alkaline phosphatase, β-galactosidase, β-glucuronidase, α-glucosidase, N-acetyl-β-glucosaminidase, urease, liquidification activities of gelatin, esculin usage, ribose consumption, xylose consumption, mannitol consumption, maltose consumption, galactose consumption, saccharose consumption, and glycogen consumption. The results of these tests concluded that the newly isolated strain belonged to the genus, *Pseudomonas* according to Bergey's manual (8th edition).

Base sequence of DNA coding 16s ribosomal RNA was also determined, and the sequence was compared to those of known bacterial strains. The results showed that the newly isolated strain was classified genus: *Pseudomonas,* and species: *citronellosis*. As the strain is new, the strain is named *Pseudomonas citronellosis* GEA.

Example 6

Optimization of Culture Conditions of *Pseudomonas citronellosis* GEA

Growth conditions of *Pseudomonas citronellosis* GEA were tested using carbon sources other than that described in Example 1 (the carbon source is theanine). Glycerol showed the result better than glutamine, glutamic acid, and glucose as carbon sources. Comparisons of various concentration of glycerol showed that 3% gave best cell-free extract with highest theanine synthesis activity. The optimum concentration of yeast extract was also tested and 0.3% of yeast extract showed the best cell-free extract having the highest theanine synthesizing activity.

TABLE 2

|  |  | Glycerol conc. 1% | Glycerol conc. 2% | Glycerol conc. 3% |
| --- | --- | --- | --- | --- |
| yeast extract 0.1% | theanine synthesis | 1.02 | 1.01 | 1.05 |
|  | glutamic acid synthesis | 0.34 | 0.38 | 0.41 |
| yeast extract 0.3% | theanine synthesis | 1.21 | 3.33 | 4.35 |
|  | glutamic acid synthesis | 0.43 | 0.25 | 0.30 |
| yeast extract 0.5% | theanine synthesis | 1.18 | 1.33 | 2.02 |
|  | glutamic acid synthesis | 0.54 | 0.45 | 0.48 | unit: mM/(h · mg)

Example 7

Optimization of Enzymatic Reaction Using Cell-Free Extract of *Pseudomonas citronellosis* GEA Comparative studies of glutamine and ethylamine concentrations under the conditions described in Example 1 with cell-free extract of *Pseudomonas citronellosis* GEA showed that 0.3M glutamine and 0.9M ethylamine were the optimum concentrations for theanine synthesis.

TABLE 3

|  | 0.2M glutamine | | 0.3M glutamine | | 0.4M glutamine | |
| --- | --- | --- | --- | --- | --- | --- |
| Ethylamine | The | Glu | The | Glu | The | Glu |
| 0.3M | 74.7 (72) | 10.7 | 98.3 (72) | 13.7 | 80.0 (48) | 33.3 |
| 0.6M | 81.6 (60) | 5 | 147 (72) | 8.1 | 115 (72) | 19.1 |
| 0.9M | 157 (60) | 3.1 | 166 (48) | 6.6 | 120 (72) | 6.2 |
| 1.2M | 155 (72) | 2.7 | 160 (60) | 5.2 | 97.1 (72) | 4.4 |

The: theanine,
Glu: glutamic acid,
( ): reaction period (hours),
unit: mM

Example 8

Production of Theanine with *Pseudomonas citronellosis* GEA

One hundred and eighty gram of bacterial cells were obtained by culturing *Pseudomonas citronellosis* GEA in 20 L medium containing 3.0% glycerine, 0.3% yeast extract, 0.05% $KH_2PO_4$, 0.05% $K_2HPO_4$, and 0.03% $MgSO_4 \cdot 7H_2O$ in 30 L fermenter (30° C., 2000 rpm). The cells were harvested by centrifugation and washed.

Ten gram of the prepared cells were used for enzymatic reaction in 0.3M glutamine, and 0.9M ethylamine at 30° C. and pH 10. Forty grams of theanine were obtained from 1 liter after incubating at 30° C. for 24 hours. Theanine was extracted from the reaction mixture by eliminating cells first and fractionated by passing through Dowex50×8 and Dowex 1×2 columns serially. The theanine fraction was crystallized and washed with ethanol.

The fraction had the same mobilities as standard theanine in amino acid analyzer and in paper chromatography. Hydrolysis of the fraction with chloric acid or glutaminase produced an equal molar ratio of glutamic acid and ethylamine. The hydrolysis of the fraction with glutaminase showed that the ethylamine was located at γ-position. The glutamic acid was shown L-form by glutamic acid hydrogenase (GluDH). IR spectrum of the fraction was identical to that of the standard as shown in FIG. 1. The isolated substance was confirmed theanine by these results.

Example 9

Production of Theanine With Immobilized Glutaminase from *Pseudomonas citronellosis* GEA (1) Preparation of Cell-free Extract One hundred and sixty gram of the cell pellet obtained in Example 8 was washed and resuspended in 2 liter of potassium phosphate buffer (30 mM, pH 7.0). Cell-free extract was obtained by sonicating the cell suspension at 5° C.~20° C.

(2). Ammonium Sulfate Fractionation

Ammonium sulfate was added to the cell-free extract stated in (1) and the pH was adjusted to 7 with 7% aqueous ammonia. At 35% saturation, precipitate was removed by centrifugation. Ammonium sulfate was added further to the supernatant to 90% saturation. The sonicater was left overnight and, precipitate was recovered by centrifugation after leaving overnight. Dialysed enzyme preparation was obtained by dissolving the precipitate in 0.01M potassium phosphate buffer, and dialysed against the same buffer.

(3) Purification of the Enzyme by Passing Through DEAE-cellulose Column Chromatography The dialysed enzyme preparation obtained in (2) was bufferized with 0.01M potassium phosphate. The enzyme was adsorbed to DEAE-cellulose column (15×60 cm), and eluted with the same buffer containing 0.1M NaCl. Eight hundred milligrams of partially purified glutaminase was obtained.

(4) Preparation of Immobilized Glutaminase

Commercial carrier particles, chitopearl 3510 (Fuji Spinning Co., Ltd.), was thoroughly washed and buffered with 0.1M sodium phosphate (pH 6.8). Two gram of the chitopearl was resuspended in 5 ml of 20 mM sodium phosphate containing 35 mg of the partially purified enzyme obtained in (3), and the suspension was stirred at 4° C. overnight. The enzyme and chitopearl were bridged by adding glutaraldehyde to the final concentration of 2.5% (V/V) and the mixture was left at 4° C. for 3 hours. The resultant immobilized enzyme was washed thoroughly with 0.1M sodium phosphate (pH 6.8) and stored at 4° C.

(5) Enzymatic Reaction of the Immobilized Glutaminase

Yield of theanine was 65% when the substrates (4% glutamine, 25% ethylamine, pH 10.0) was passed through a column of the immobilized enzyme prepared in (4) at 30° C., solvent velocity=0.2. Theanine was isolated and purified by consecutive treatments with Dowex 50×8 column, Dowex 1×2 column and ethanol treatment.

Analyses of the isolated product by amino acid analyzer and paper chromatography showed that the pattern was identical to the standard. Hydrolysis with chloric acid or glutaminase produced glutamic acid and ethylamine at 1:1 molar ratio. The hydrolysability of the product with glutaminase showed that ethylamine locates at γ-position of glutamic acid. The glutamic acid produced by the hydrolysis was confirmed L-form with glutamic acid dehydrogenase (GluDH). IR analyses showed that the spectra of the isolated product was identical to that of the standard theanine as is shown in Example 8. These results showed that the isolated product is theanine.

The invention claimed is:

1. A method for producing theanine comprising the steps of:

reacting glutamine and ethylamine by *Pseudomonas citronellosis* GEA to produce theanine, wherein said *Pseudomonas citronellosis* GEA is FERM BP-8353.

2. The method according to claim 1, wherein a pH for reacting the glutamine and ethylamine is in a range of 9 to 12.

3. A method for producing theanine comprising the steps of: extracting glutaminase from *Pseudomonas cintronellosis* GEA FERM BP-8353; and reacting glutamine and ethylamine by the glutaminase to produce theanine.

4. The method according to claim 3, wherein a pH for reacting the glutamine and ethylamine is in a range of 9 to 12.

* * * * *